(12) United States Patent
Hancock et al.

(10) Patent No.: US 6,534,504 B1
(45) Date of Patent: Mar. 18, 2003

(54) INDAZOLYLOXY PROPANOLAMINES FOR IMPROVING LIVESTOCK PRODUCTION

(75) Inventors: Deana Lori Hancock, Carthage, IN (US); Randall Bruce Hopkins, Indianapolis, IN (US); Michael Eugene Quimby, Indianapolis, IN (US); Andrew Jason Wuethrich, Peoria, IL (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/110,890

(22) PCT Filed: Nov. 13, 2000

(86) PCT No.: PCT/US00/30129

§ 371 (c)(1),
(2), (4) Date: Apr. 16, 2002

(87) PCT Pub. No.: WO01/36390

PCT Pub. Date: May 25, 2001

Related U.S. Application Data

(60) Provisional application No. 60/165,593, filed on Nov. 15, 1999.

(51) Int. Cl.[7] .................... A61K 31/5377; A61P 43/00; C07D 231/56; C07D 413/14

(52) U.S. Cl. .................... 514/234.5; 514/403; 544/131; 546/275.7; 548/361.1

(58) Field of Search ...................... 544/131; 546/275.7; 548/361.1; 514/234.5

(56) References Cited

U.S. PATENT DOCUMENTS

| 4,346,093 A | 8/1982 | Friebe et al. |
| 5,013,761 A | 5/1991 | Beedle et al. |

FOREIGN PATENT DOCUMENTS

| EP | 0 714 883 A | 6/1996 |
| EP | 0 764 640 | 3/1997 |
| EP | 0 921 120 A | 6/1999 |
| WO | WO 97/10825 | 3/1997 |
| WO | WO 01/35947 | 5/2001 |
| WO | WO 01/36412 | 5/2001 |

*Primary Examiner*—Robert W. Ramsuer
(74) *Attorney, Agent, or Firm*—John C. Demeter

(57) ABSTRACT

Disclosed is compound represented by Structural Formula (I), wherein Ring A, Ring B and Ring C are independently substituted or unsubstituted. R1 and R2 are independently a C1–C4 straight chained or branched alkyl group. Also disclosed is a method of increasing the quantity and improving quality of meat obtained from a livestock animal. The method comprises administering to the animal an effective amount of one or more compounds represented by Structural Formula (I).

20 Claims, No Drawings

INDAZOLYLOXY PROPANOLAMINES FOR IMPROVING LIVESTOCK PRODUCTION

This application claims the benefit of provisional application No. 60/165,593 filed Nov. 15, 1999.

BACKGROUND OF THE INVENTION

An important goal in animal husbandry is to develop biologically active agents which can increase the quantity and improve the quality of meat obtained from livestock animals.

"Increasing the quantity" of food obtained from livestock animals refers to, inter alia, promoting the growth of livestock animals, increasing the efficiency of feed utilized in raising livestock animals and/or enhancing the production of lean body mass in livestock animals. Biologically active agents with these attributes are commonly referred to as "anabolic agents".

"Improving the quality" of food obtained from livestock animals refers to, inter alia, reducing the quantity of subcutaneous fat in meat and, in poultry, the size of the abdominal "fat pad". Subcutaneous fat can cause elevated cholesterol and triglyceride levels in individuals who consume large quantities of meat, has minimal nutritional value and decreases the overall yield of meat. Therefore, the reduction or elimination of this type of fat from meat is desirable. On the other hand, intramuscular fat, commonly referred to as "marbling", contributes positively to the flavor of meat and maintains a high Quality Grade. Marbling is therefore considered a desirable quality. Biologically active agents which are lipolytic can reduce subcutaneous fat while retaining the intramuscular fat.

Certain publications have appeared generally disclosing arylpropanolamines such as U.S. Pat. No. 5,013,761 and WO 97/10825. There continues to be a need for the development of agents which are anabolic and lipolytic to improve the economics of meat production by increasing the yield and improving the quality of meat obtained from livestock animals. Further increases in profitability could be achieved by the development of long-lasting anabolic/lipolytic agents which, because they require less frequent dosing, are more convenient and economical to use.

BRIEF SUMMARY OF THE INVENTION

It has now been found that indazolyloxy propanolamimines such as those represented by Structural Formula (I) and (III) below are both anabolic and lipolytic when administered to livestock (Example 7 and Table 1). It has also been found that the anabolic and lipolytic effects of these compounds are longer lasting than other aryloxy propanolamines. Specifically, the percent decrease in serum urea nitrogen level (SUN) after forty-eight hours and the increase in non-esterified fatty acid levels (NEFA) after twenty-four hours in cattle treated with the indazolyloxy propanolamines of the present invention have been found to be significantly greater than for other aryloxy propanolamines (see Example 8 and Table 2). The percent decrease in SUN is indicative of anabolic activity and the increase in NEFA is indicative of lipolytic effects. Based on these results, novel compounds and novel methods of improving meat production from livestock animals are disclosed herein.

One embodiment of the present invention is a compound represented by Structural Formula (I):

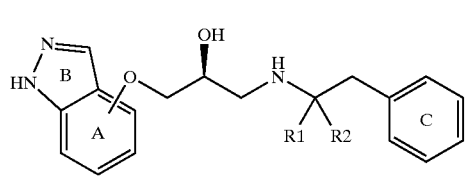

and physiologically acceptable salts thereof; where R1 and R2 are independently —H or a C1–C4 straight chained or branched alkyl group;

Ring A, Ring B and Ring C are independently substituted or unsubstituted, provided, however, that Ring C is not substituted in the para position with a group represented by Structural Formula (II):

R3 and R4 are independently —H, a straight or branched C1–C4 alkyl or, taken together with the nitrogen atom to which they are bonded, form a non-aromatic heterocyclic ring, and Ring D is substituted with zero, one, two or three additional substituents.

Another embodiment of the present invention is a compound represented by Structural Formula (III):

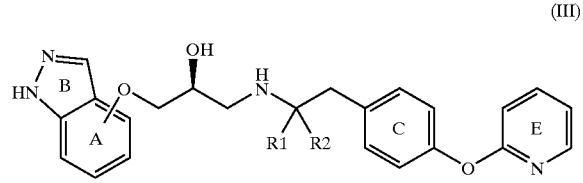

and physiologically acceptable salts thereof; where

R1 and R2 are independently —H, a C1–C4 straight chained or a branched alkyl group;

Ring A, Ring B, Ring C and Ring E are independently substituted or unsubstituted, provided, however, that Ring E is not substituted in the position meta to —N— and ortho to the carbon bonded to oxygen with —CONR3R4;

R3 and R4 are independently —H or a straight or branched chain C1–C4 alkyl group or, taken together with the nitrogen atom to which they are bonded, form a non-aromatic heterocyclic ring.

Another embodiment of the present invention is a method of increasing the quantity and improving the quality of meat obtained from a livestock animal. The method comprises administering to the animal an effective amount of one or more compounds represented by Structural Formula (I). Another embodiment of the present invention is a method of increasing the quantity and improving quality of meat obtained from a livestock animal. The method comprises administering to the animal an effective amount of one or more compounds represented by Structural Formula (III).

The indazolyloxy propanolamines of the present invention have both anabolic and lipolytic activity and can therefore be administered to livestock to increase the output of meat and to decrease its fat content. Moreover, the duration of the anabolic and lipolytic activity of these indazolyloxy propanolamines is longer in vivo than other structurally related aryloxy propanolamines. Consequently, indazolyloxy propanolamines are more convenient and economical to use than other aryloxy propanolamines because indazolyloxy propanolamines need to be administered less frequently and/or at lower doses. The compounds of the present invention are intended for the treatment of healthy animals.

DETAILED DESCRIPTION OF THE INVENTION

The present invention is directed to a compound represented by Structural Formula (I) and (III). Also included is a method of improving livestock production by administering one or more compounds of the present invention to the livestock.

In a preferred embodiment, the compound is represented by Structural Formula (IV):

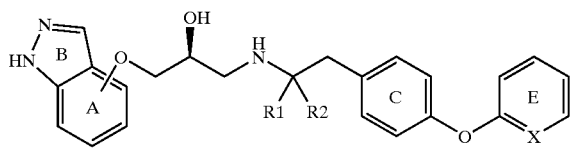

(IV)

Ring A, Ring B, Ring C, R1 and R2 are as described above for Structural Formula (I). Ring E is substituted or unsubstituted.

X is —CH— or —N—.

In Structural Formula (IV), R1 and R2 are preferably methyl and Rings A–C have no further substitution.

In a preferred embodiment, the compound of the present invention is represented by Structural Formula (V):

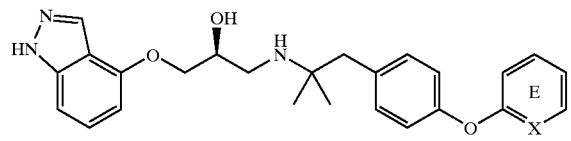

(V)

X is —N— or —CH—.

Ring E is substituted or unsubstituted. Examples of suitable substituents for Ring E include halo, —CN, —OR5, C1–C4 alkyl, C1–C4 haloalkyl, —CO$_2$R5, —CONR6R7, —CONH(C1–C4 alkyl), —SR5, —CSNR6R7, —CSNR6R7, —SO$_2$R5, —SO$_2$NR6R7, —SOR5, —NR6R7. Preferred substituents are —CN, —CONH$_2$, —SO$_2$CH$_3$, —SO$_2$NH$_2$ or are represented by Structural Formulas (VI) or (VII):

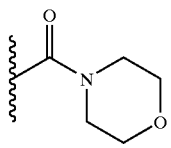

(VI)

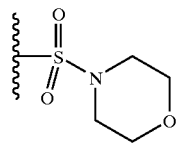

(VII)

—SR$_2$CH$_3$ is a more preferred substituent.

R5 is —H, C1–C4 alkyl or aryl.

R6 and R7 are independently —H, C1–C4 alkyl, aryl, —(CH$_2$)$_n$aryl, or combine with the nitrogen atom to which each is bound to form morpholinyl, piperidinyl, pyrrolidinyl, or piperazinyl.

n is 0, 1, 2, or 3.

In another preferred embodiment, the compound of the present invention is represented by Structural Formula (IV) or (V), provided, however, that Ring E is not substituted in the position meta to —X— and ortho to the carbon bonded to oxygen with —CONR3R4. R3 and R4 are independently —H or a straight or branched chain C1–C4 alkyl group or, taken together with the nitrogen atom to which they are bonded, form a non-aromatic heterocyclic ring.

Also included in the present invention are Compounds 1–5, shown in Tables 1 and 2.

Physiologically acceptable salts of the compounds disclosed herein, including the compounds represented by Structural Formulas (I),(III), (IV), (V) and Compounds 1–5, shown in Tables 1 and 2, are included. Salts can be formed from those compounds which comprise acidic functional groups by reacting with a suitable base. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

Because of the amine moiety, salts of the compounds disclosed herein can also be prepared by reacting with a suitable acid. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like salts.

When substituted, Rings A–E can have one, two or three substituents in addition to those shown in Structural Formulas (I)–(V). Suitable substituents are those which do not significantly decrease the anabolic and lipolytic properties of the compound. Examples of suitable substituents include halogens, hydroxy, —OR', —SR', —S(O)R', —S(O)$_2$R', —COOR', —C(O)R', —CN, —NO$_2$, —OCONR'R", —OCONHR', —NHCOOR', —NR"COOR', —NHR', —NR'R", —CN, C1–C4 alkyl, C1–C4 haloalkyl, —CONR'R", —CONHR', —CSNR'R", —CSNR'R", —SO$_2$NR'R". R' and R" are independently —H, C1–C4 alkyl or aryl. In addition, when R' and R" are bonded to the same nitrogen atom (e.g, —NR'R", —CONR'R" or —OCONR'R"), then R and R', taken together with the nitrogen atom, can form a non-aromatic heterocyclic ring.

Aryl groups include carbocyclic aromatic groups such as phenyl, 1-naphthyl, 2-naphthyl, 1-anthracyl and 2-anthracyl, and heteroaryl groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aryl groups also include fused polycyclic aromatic ring systems in which a carbocyclic aromatic ring or heteroaryl ring is fused to one or more other heteroaryl rings. Examples include 1-benzimidazolinyl, 2-benzimidazolonyl, 1-benzimidthioazolinyl, 2-benzimidthioazolonyl, 1-carbazolyl, 2-carbazolyl, 3-carbazolyl, 4-carbazolyl, 3-indazolyl, 4-indazolyl, 5-indazolyl, 6-indazolyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 2-quinolinyl, 3-quinolinyl, 1-isoquinolinyl, 3-quinolinyl, 1-isoindolyl and 3-isoindolyl. Also included within the scope of the term aryl group, as it is used herein, is a group in which one or more carbocyclic aromatic rings and/or heteroaromatic rings are fused to a cycloalkyl or non-aromatic heterocyclic ring.

Non-aromatic heterocyclic rings are non-aromatic carbocyclic rings which include one, two or three heteroatoms selected from nitrogen, oxygen and sulfur in the ring that will afford a stable structure. The ring can be five, six, seven or eight-membered. Examples include 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl.

As used herein, aliphatic groups include straight chained, branched or cyclic C1–C20 hydrocarbons which are completely saturated or which contain one, two or three units of unsaturation.

Suitable substituents on an aliphatic group, aryl group (carbocyclic and heteroaryl), non-aromatic heterocyclic ring or benzyl group are those which do not significantly reduce the anabolic effects or alter the lipolytic effects of the compound. Examples include —OH, halogen (—Br, —Cl, —I and —F), —OR, —O—COR, —CN, —NO$_2$, —COOH, —NH$_2$, —NHR, —NR$_2$, —COOR, —COR, —CHO, —CONH$_2$, —CONHR, —CONR$_2$, —SH, —SR and —NH—C(=NH)—NH$_2$. R is C1–C6 alkyl, benzyl, or phenyl.

A substituted non-aromatic heterocyclic ring can also have =O, =S, =NH or =NR where R is as defined above as a substituent. A substituted aliphatic, substituted aromatic, substituted non-aromatic heterocyclic ring or substituted benzyl group can have one, two or three substituents.

In the structural formulas depicted herein, the bond by which a chemical group or moiety is connected to the remainder of the molecule or compound is indicated by the following symbol:

⟨

For example, the corresponding symbol in Structural Formula (II) indicates the bond by which the oxygen of the pyridyloxy group is connected to Ring C of Structural Formula (I).

The present invention includes solvates of the compounds of Structural Formula I and the physiologically acceptable salts thereof. A particular compound of the present invention or a physiologically acceptable salt thereof may form solvates with water or common organic solvents. Such solvates are included within the scope of compounds of the present invention.

In addition, it will be appreciated that diastereomers exist for the compounds of Structural Formula I and, depending on the substituents, further diastereomers may exist. The compounds of the present invention include mixtures of two or more diastereomers as well as each individual stereoisomer.

It will also be appreciated that some of the heterocycles may exist in tautomeric forms. All such forms are included within the scope of the present invention.

As used herein, "crystallizing" refers to providing a solvent or solvent mixture in which the indazolyloxy propanolamine compound is highly soluble and in which an ammonium salt(s) thereof is insoluble or only slightly soluble. The compound is dissolved in the solvent or solvent mixture and then converted to the ammonium salt by the addition of at least one equivalent of the appropriate acid, after which the ammonium salt precipitates. To minimize contamination of the precipitated product, between about 1.0 and about 1.1 equivalents of acid are preferably used. Impurities present in the indazolyloxy propanolamine are preferably highly soluble in the solvent or solvent mixture, resulting in a precipitated salt which is purified relative to the free base prior to precipitation. More preferably, the precipitated compound is crystalline.

Purification by acidic (or basic) extraction refers to dissolving a compound with a basic functional group such as an amine (or a compound with an acidic functional group, such as a carboxylic acid) in aqueous or alcoholic acid (or aqueous or alcoholic base, in the case of a compound with an acidic functional group). The aqueous solution can then be washed with organic solvents that are not miscible with water to remove organic impurities. The pH of the solution is then adjusted to the isoelectric point of the compound, thereby precipitating the compound or allowing its extraction into an organic solvent.

Purification by precipitation at the isoelectric point refers to adjusting the pH of an aqueous solution of a compound with both an acidic and basic functional group (e.g., an amino acid) to its isoelectric point, thereby causing the compound to precipitate from solution. "Isoelectric pH" is the pH at which the compound is electrically neutral and therefore least soluble in aqueous solution. Preferably, impurities present in the compound are highly soluble at the isoelectric point. As a result, the precipitated compound is purified relative to the compound prior to precipitation. More preferably, the precipitated compound is crystalline. Optionally, a compound with both an acidic and basic functional group can be purified by both by acidic (or basic) extraction and by precipitation at its isoelectric point.

Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The method of the present invention is preferably used with avians.

An "effective amount" of a compound of the present invention is the quantity which, when administered to a livestock animal, increases the quantity of meat and/or quality of meat obtained from the animal.

Increasing the quantity of meat obtained refers to promoting a greater amount of growth in the animal with a treatment compared with the absence of the treatment. Alternatively, increasing the quantity of meat obtained refers to promoting formation of lean body mass. The formation of lean body mass is promoted, for example, when there is a higher ratio of muscle to fat as a result of a treatment than in the absence of the treatment. Alternatively, increasing the quantity of meat obtained refers to improving the efficiency of utilization of food. Food utilization is more efficient when there is a greater body weight gain per a given amount of feed consumed by an animal as a result of a treatment than in its absence. Thus, increasing the quantity of meat obtained from a livestock animal generally results in an improvement in the economics, e.g., in increase in the profitability of producing meat.

Increasing the quality of meat refers to an improvement in carcass quality of the animal. Improved carcass quality refers, for example, to the formation of less fatty tissue (subcutaneous fat), to a decreased size of the fat pad in poultry and/or to greater leanness (improved yield). Thus, improved carcass quality generally results in meat that is more healthy to consume, e.g., is less likely to cause elevated cholesterol and/or triglyceride levels. Improving the quality of meat can also improve the economics and increase the profitability of producing meat because high quality grade meat can command higher selling prices at market.

The effective amount to be administered will vary somewhat depending upon the particular animal species being treated and the particular active ingredient employed, but generally will be from about 0.5 to about 1000 parts per million (ppm: milligrams compound per kilogram food) of total daily feed intake. Such amount will provide a dosage of about 0.02 to about 50 mg/kg. A preferred embodiment employs about 0.5 to about 200 ppm, and more preferably from about 1 to about 40 ppm. For example, when practicing the method in animals such as poultry, the compound will be added to the daily feed ration at about 2 to 100 parts per million of the daily feed ration.

The method of the present invention is preferably practiced by orally administering an effective amount of a compound of the present invention to a livestock animal. Other routes of administration can be employed, for instance intranasal (e.g., by intranasal misting device), in ovo or subcutaneous, intramuscular or intravenous injection; however, such routes are less practical.

For oral administration, a compound of the present invention is preferably admixed with suitable carriers or diluents commonly employed in animal husbandry. Animal feedstuffs comprising a compound of the present invention are provided as a further embodiment of this invention. Typical carriers and diluents commonly employed in such feedstuffs include corn meal, corncob grits, soybean meal, alfalfa meal, rice hulls, soybean mill run, cottonseed oil meal, bone meal, ground corn, corncob meal, wheat middlings, limestone, dicalcium phosphate, sodium chloride, urea, distillers dried grain, vitamin and/or mineral mixes, cane molasses or other liquid carriers and the like. Such carriers promote a uniform distribution of the active ingredient, and more typically about 20 to about 98 percent by weight.

While the preferred method for orally administering the compounds of the present invention is via the daily feed rations, the compounds can be incorporated into salt blocks and mineral licks, as well as being added directly to link tank formulations or drinking water for convenient oral consumption. The compounds can additionally be formulated with polymorphous materials, waxes and the like for long-term controlled release, and administered to animals as a bolus or tablet only as needed to maintain the desired daily payout of active ingredient. Compounds can also be administered orally by gavage treatment and/or applied transdermally.

For parenteral administration, the compounds of the present invention can be admixed with conventional carriers such as water, propylene glycol, polyethylene glycols, n-methyl pyrrolidone, glycerol formal, corn oil, sesame oil, calcium stearate, polymeric materials and the like. Such formulations can be molded into pellets and administered as an injection or as a slow-release subcutaneous implant, sustained rumen delivery device or intranasal device. Such administrations can be made as often as needed to ensure the proper dosing of active ingredient to obtain the desired rate of growth promotion and improvement in leanness and feed efficiency.

The compounds of the present invention can be prepared by procedures disclosed in WO 97/10825 to Bell et al., WO 98/09625 to Crowell et al., U.S. Pat. Nos. 5,808,080 and 6,046,227. The entire teachings of these references are incorporated herein by reference. A reaction scheme for preparing these compounds is shown below:

Scheme

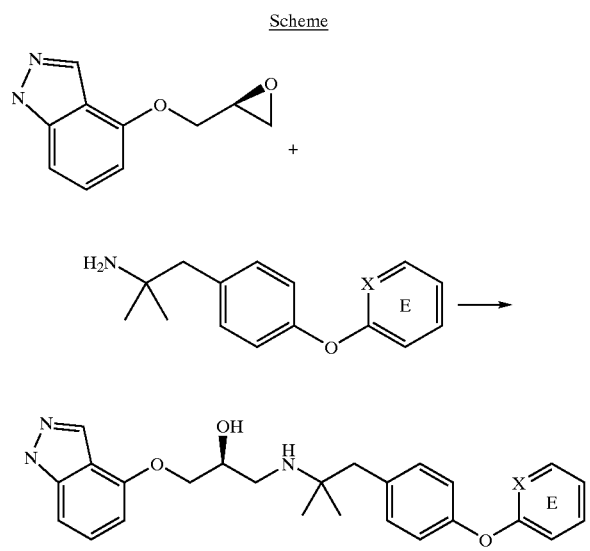

X and Ring D in the Scheme are as described above.

The amination of the epoxides in the Scheme is carried out under conditions known in the art for this type of reaction. For example, the epoxide may be combined with the amine in an alcohol, preferably ethanol at room temperature, to the reflux temperature of the reaction mixture. For example, the reaction is carried out under conditions generally described in Atkins et al., *Tetrahedron Letters* 27:2451 (1986) the entire teachings of which are incorporated herein by reference. An example of specific conditions for reacting an epoxide with an amine is provided in Example 6.

Substituents which interfere with the reaction shown in the Scheme can be present, provided that they are first converted to a protected form. Suitable protecting groups are known to those skilled in the art and are disclosed in Green and Wuts, *"Protecting Groups in Organic Synthesis"*, John Wiley and Sons, 1991, the teachings of which are incorporated herein by reference.

An alternative method of preparing the compounds of the present invention involves deprotecting a cyclic sulfate-containing compound to reveal hydroxy substituents, and comprises combining the cyclic sulfate-containing compound with a trialkylsilyl halide in a solvent for a time sufficient to deprotect the hydroxyl group.

Specifically, the process comprises reacting a compound of the formula (VIII):

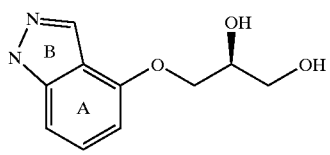

(VIII)

with thionyl halide in a solvent for a time sufficient to yield a sulfite compound of the formula (IX):

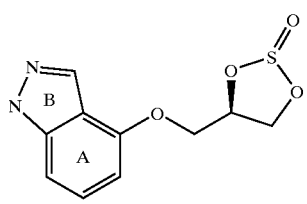

(IX)

where Ring A and Ring B are as described above.

Suitable thionyl halides include thionyl bromide and thionyl chloride. Thionyl chloride is preferred. Typically, 2 equivalents of thionyl halide are used per mole of compound (VIII).

Any solvent can be used in this step, so long as it does not interfere with the reaction. THF is preferably used. The reaction is typically conducted until product is obtained, generally for about 120 to 240, preferably 180, minutes. The reaction can be conducted at any temperature, but generally is conducted at a temperature less than about 0° C., preferably from about −10 to 0° C., more preferably from about −10 to −5° C., most preferably from about −9 to −8° C.

In a preferred embodiment, the NH group in the 1H-indazole ring is first N-protected prior to conversion of the compound to the corresponding sulfate. Selection of the protecting group is preferably made such that it can be removed under the same conditions as for removing the sulfate group to reveal a hydroxy group.

Conditions for N-protecting the nitrogen atoms depend on the particular protecting group chosen. Suitable reaction conditions are described in "Protective Groups in Organic Synthesis," Peter G. M. Wuts (Editor), Theodora W. Greene, 3rd ed. (April 1999), Vch Pub.

Thereafter, compound (IX) can be converted into corresponding sulfate compound of the formula (X):

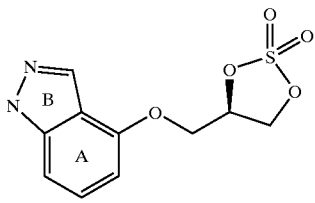

(X)

where Ring A and Ring B are as described above.

Suitably, the conversion comprises combining sulfite compound (IX) with a catalytic amount of a ruthenium compound and an oxidizing agent in solvent for a time sufficient to oxidize said sulfite compound (IX) to a sulfate compound (X).

Suitable ruthenium compounds include ruthenium chloride or ruthenium oxide. Generally, about 0.001 to 0.25 equivalents of ruthenium compound are used per mole of sulfite compound (IX).

Suitable oxidizing agents include sodium periodate, sodium hypochlorite, sodium bromate, calcium hypochloride, sodium chlorate or ozone. Generally, about greater than about 2.0, preferably 2.5, equivalents of oxidizing agent are used per mole of sulfite compound (IX).

The conversion is typically conducted in any solvent that would not interfere with the reaction, such as $CCl_4$, $CHCl_3$, $CH_3CN$, or water or mixtures thereof. The conversion is typically conducted for about 30 to 120, preferably 60, minutes. Preferably, the conversion is conducted in a mixture of $CHCl_3$, $CH_3CN$ and water. The conversion is typically conducted at a temperature of from about −10 to 25° C.

Thereafter, the sulfate compound (X) can be reacted with a primary amine of the formula (XI):

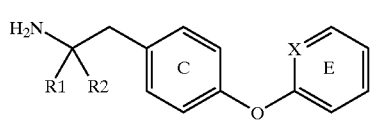

(XI)

where X, Ring C and Ring E are as described above, in solvent for a time sufficient to yield a compound (XII):

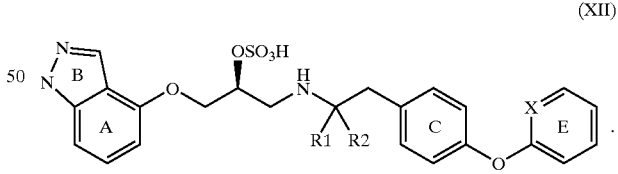

(XII)

Typically, about 0.9 to 2 equivalents of amine are used per mole of sulfate compound (X). Preferably, about 0.9 to 1.1 eq. are used. Most preferably, about 1.0 eq. (a stoichiometric amount) of amine is used.

Typically, any solvent can be used in this step, as long as it does not interfere with the reaction. Preferably, the reaction is conducted in $CH_3CN$. The reaction is typically conducted for about 60–180, preferably 120, minutes at a temperature of from about 78 to 85° C.

Finally, the compound (XII) can be combined with trialkylsilyl halide in solvent for a time sufficient to yield compound (IV):

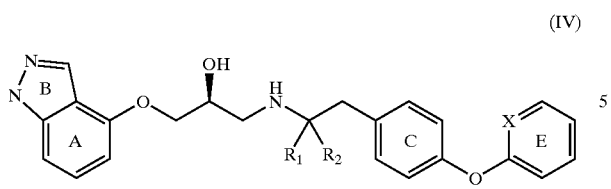

(IV)

where R1, R2, X, Ring A, Ring B, Ring C, and Ring E are as described above.

Suitable trialkylsilyl halides include trialkylsilyl iodide, trialkylsilyl bromide or trialkylsilyl chloride. Preferably, the trialkylsilyl halide is trimethylsilyl iodide.

The reaction may be carried out in any solvent, so long as the solvent does not interfere with the reaction. Preferably, the solvent is an aprotic solvent such as carbon tetrachloride, acetonitrile, dimethyl sulfoxide, dimethylformamide, sulfolane, tetrahydrofuran, diethyl ether, methyl-t-butyl ether, 1,2-dimethoxy-ethane, dioxane, chloroform, methylene chloride, toluene or acetone or mixtures thereof.

The reaction is typically conducted for 5–25, preferably 15, minutes at a temperature of less than 0° C., preferably −10 to 0° C., most preferably −9 to −8° C.

A method of preparing the compounds of the present invention involves formation of salts of novel indazolyloxy propanolamines in which the amine group is substituted with an alkyl 2-[4-(2-yl-2-methylpropyl)phenoxy]pyridinecarboxylate group (hereinafter "indazolyloxy propanolamine esters"). These indazolyloxy propanolamine esters can be readily crystallized in high yield and in high purity, substantially free (typically less than 1 ppm) of epoxide precursors. In addition, the corresponding carboxylic acids of indazolyloxy propanolamine esters (hereinafter "indazolyloxy propanolamine carboxylic acids") can be purified by precipitation at their isoelectric point in high yield and high purity. Both indazolyloxy propanolamine esters and carboxylic acids can be prepared in high yield from readily accessible starting materials.

This method can be used to prepare an indazolyloxy propanolamine ester represented by Structural Formula (XIII):

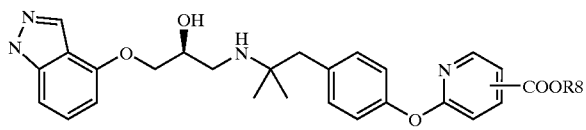

(XIII)

and ammonium salts thereof.

R8 is a C1 to C6 straight or branched chain alkyl group or a C7 to C9 substituted or unsubstituted aralkyl group. Preferably, R8 is methyl or ethyl.

The method comprises the step of reacting an epoxide starting material with an amine starting material. The epoxide starting material is represented by Structural Formula (XIV):

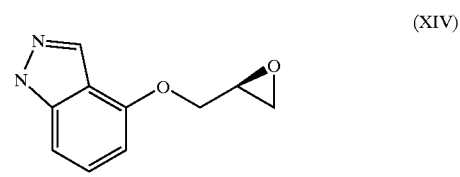

(XIV)

and the amine starting material is represented by Structural Formula (XV):.

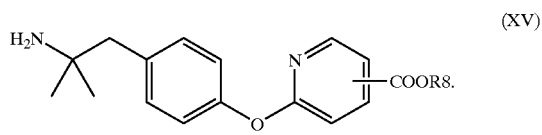

(XV)

This method of can also be used to prepare an indazolyloxy propanolamine carboxylic acid or a carboxylate salt thereof from an indazolyloxy propanolamine ester represented by Structural Formula (XIII). The indazolyloxy propanolamine carboxylic acid is represented by Structural Formula (XVI):

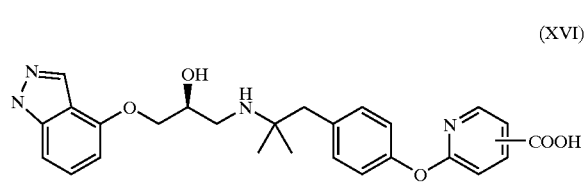

(XVI)

The method comprises the step of hydrolyzing the —COOR8 group of the indazolyloxy propanolamine ester.

Because of the amine moiety present in the indazolyloxy propanolamines esters disclosed herein, ammonium salts of these compounds can be prepared by reacting with a suitable acid. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate and mandelate salts.

Carboxylate salts can be formed from the indazolyloxy propanolamines acids disclosed herein which have a carboxylic acid functional group by reacting with a suitable base. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, sodium hydroxide, lithium hydroxide, potassium hydroxide, methylamine, diethylamine, ethylenediamine, cyclohexylamine, ethanolamine and the like.

Preferred carboxylate salts of the compound represented by Structural Formula (XVI) include alkali metal carboxylate salts such as the sodium carboxylate salt, the potassium carboxylate salt and the lithium carboxylate salt.

The preparation of the indazolyloxy propanolamine ester represented by Structural Formula (XIII) from the epoxide and amine represented by Structural Formulas (XIV) and (XV), respectively, is generally carried out in a solvent at room temperature to the reflux temperature of the reaction mixture. Temperatures of 40–140° C. are generally preferred. The solvents that may be used in the reaction include: alcoholic solvents, such as methanol, ethanol or isopropanol, (with the preferred solvent corresponding to the particular ester being used in the reaction to prevent transesterification); aromatic solvents, such as benzene, toluene, xylenes, chlorobenzene, dichlorobenzene, other haloaromatics, nitrobenzene, benzonitrile, or trifluoromethylbenzene; or dipolar aprotic solvents, such as dimethylsulfoxide (DMSO), N,N-dimethylacetamide (DMAC) or N,N-dimethylformamide; or other solvents where the reagents are soluble and the temperature can be elevated to the range previously described. Equimolar amounts of epoxide and amine can be used. Alternatively, up to about a five fold excess of one reagent is used. Preferably, however, between about 1.1 to about 2.0 equivalents of amine relative to epoxide is preferred.

Indazolyloxy propanolamine esters, prepared as described above, can be purified by any suitable means, including by converting to a suitable ammonium salt and crystallizing, as described above.

Amine starting materials can be prepared as generally described in Examples 3 and 4. A phenoxide salt of the alkylamino phenol represented by Structural Formula (XVII) is reacted with a 2-halo pyridine ester represented by Structural Formula (XVIII):

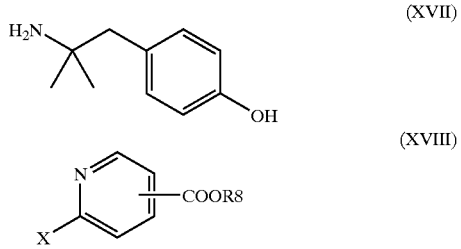

R8 in Structural Formula (XVIII) is as described for Structural Formula (XIII). X is a halo group. The coupling reaction and the preparation of the compound represented by Structural Formula (XVII) can be carried out according to procedures described in the aforementioned WO 97/10825 to Bell et al., WO 98/09625 to Crowell et al., U.S. Pat. Nos. 5,808,080 and 6,046,227.

Generally, the reaction may be carried out by mixing the alkylamino phenol with a base in the presence of the 2-halopyridine ester. Equimolar amounts of the starting materials are preferably used. However, molar excesses up to about five or ten fold of one starting material relative to the other can be used. The coupling is performed by mixing the amino phenol with a base in a suitable solvent or solvent system. The reaction can be carried out at temperatures as low as room temperature, but is preferably carried out by heating the mixture at reflux while azeotropically removing water formed during the deprotonation step. The 2-halopyridine ester is then added and the reaction continued until the reaction is complete.

Suitable solvents include dipolar aprotic, ethereal, and aromatic solvents, as well as combinations thereof. Dipolar aprotic solvents include solvents such as DMSO, N,N-dimethylacetamide, N-methylpyrrolidinone, 1,3-dimethyl-2-imidazolindinone (DMI), 1,3-dimethyl-3,4,5,6-tetrahydro-2(1H)-pyrimidinone (DMPU) with a lower boiling solvent to azeotropically remove water such as benzene, toluene, isooctane, xylenes or other solvents capable of forming binary azeotropes with water but which are inert under the reaction conditions. Other suitable compounds for azeotropic removal of water may be found in Advances In Chemistry Series 116—Azeotropic Data III, American Chemical Society: Washington D.C., 1973. Ethereal solvents include tetrahydrofuran, dioxane and 1,2-dimethoxyethane. Aromatic solvents include benzene, toluene, chlorobenzene, anisole and 1,2-dichlorobenzene. Preferred is the use of an aromatic solvent such as chlorobenzene containing 0.1–10 equivalents of a dipolar aprotic solvent such as N,N-dimethylacetamide. Suitable bases include alkali metal alkoxides, such as alkali metal methoxides, ethoxides and tert-butoxides (preferably corresponding to the alkyl group of the ester to prevent transesterification), alkali metal hydroxides, such as lithium hydroxide, sodium hydroxide and potassium hydroxide, or alkali metal carbonates, such as $Na_2CO_3$ or $K_2CO_3$. Although excesses of base up to at least about ten fold can be used, preferred is the use of stoichiometric quantities of hydroxide or alkoxide bases or 1.5–5 equivalents of $K_2CO_3$.

The preparation of the epoxide starting material represented by Structural Formula (XIV) can be carried out by reacting 4-hydroxyindazole with (2S)-(+)-glycidyl 3-nitrobenzenesulfonate in an inert solvent (e.g., acetone, methyl ethyl ketone, methyl isobutylketone, dimethyl sulfoxide, N,N-dimethylacetamide (DMAC) or DMF) and in the presence of a base. Although about equimolar amounts of the starting materials are preferred, molar excess up to about five to about ten-fold of one starting material relative to the other can also be used. Suitable bases include non-nucleophilic bases such as potassium carbonate, sodium carbonate and alkali metal alkoxides; potassium carbonate is preferred. Although an excess of base can be used, between about 1.05 and about 1.50 equivalents of $K_2CO_3$ are preferred. The reaction is carried out at temperatures ranging from about ambient temperature to about 40° C., preferably about 30° C. Other sulfonate esters can also be used (e.g., tosylate, nosylate or mesylate) as well as halides such as epibromohydrin or epichlorohydrin. The nosylate is preferred. Specific reaction conditions are described in Examples 1 and 2.

The hydrolysis of the indazolyloxy propanolamine ester represented by Structural Formula (XIII) to form the carboxylic acid represented by Structural Formula (XVI) or the carboxylate salt thereof can be carried out by any suitable means, including by procedures disclosed in Larock, R. C. Comprehensive Organic Transformations; VCH: New York, 1989, pp. 981–985; March, "Advanced Organic Chemistry", third($3^{rd}$) edition, John Wiley Sons (1985), pages 375–76 and references cited therein, the entire relevant teachings of which are incorporated herein by reference. This reaction is referred to herein as the "hydrolysis reaction".

Preferably, the hydrolysis reaction is carried out in alcoholic base such as lithium hydroxide, sodium hydroxide or potassium hydroxide in methanol or ethanol. Methanolic sodium hydroxide is preferred. The hydrolysis can be carried out with one equivalent of base relative to indazolyloxy propanolamine ester. Alternatively, an excess of base, for example, an excess up to about ten to about twenty-fold can be used to form the carboxylate salt. Preferably, the excess of base is between about zero and about 30 percent. Generally, the reaction temperature varies between room temperature and the reflux temperature of the solvent, and is typically 40–70° C. The carboxylic acid product (or carboxylate salt thereof) is isolated by conventional means, for example, by removal of the solvent in vacuo.

The indazolyloxy propanolamine carboxylic acid or carboxylate salt thereof can be purified by basic (or acidic) extraction, e.g., by dissolving in aqueous base (e.g., aqueous sodium hydroxide, potassium hydroxide or lithium hydroxide), and/or by precipitation at its isoelectric point. Preferably, the aqueous solution is extracted with one or more organic solvents which are not miscible with water to remove impurities. The pH of the aqueous solution can then adjusted to its isoelectric point with aqueous acid (e.g., aqueous HCl, $H_2SO_4$, acetic acid or a sulfonic acid), thereby causing the indazolyloxy propanolamine carboxylic acid to precipitate.

The indazolyloxy propanolamine carboxylic acids or carboxylate salts thereof can also be purified by using either cationic ion-exchange resins, such as AMB 15 (H form), 50WX2-400 (H form), or IR50S (H form) and eluting with an alcoholic solution of an alkali metal acetate, such as 6% (w/v) sodium acetate in methanol; or by using anionic ion-exchange resins, such as IRA900 (chloride form) or A21 (acetate form) and eluting with a basic solution of water and either alcohol or acetonitrile.

The individual optically active isomers of the compounds prepared by the present invention may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley Sons, 1981.

The compounds employed as initial starting materials in the synthesis of the compounds of this invention are well known and, to the extent not commercially available, are readily synthesized by standard procedures commonly employed by those of ordinary skill in the art.

The invention is illustrated by the following examples, which are not meant to be limiting in any way.

EXEMPLIFICATION

EXAMPLE 1

Preparation of 4-Hydroxyindazole

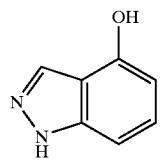

4-Hydroxyindazole was prepared according to procedures disclosed in Davies, *J. Chem. Soc.* 1955:2412 (1955) and H. D. Porter and W. D. Peterson, "Organic Synthesis", Collective Volume III, p.660. The entire teachings of these references are incorporated herein by reference. Specific conditions for preparing 4-hydroxyindazole are provided below.

A. Preparation of 4-Nitroindazole from 2-Methyl-3-Nitro-Aniline

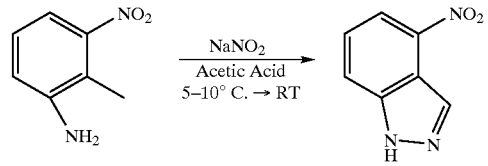

Sodium nitrite (20 grams, 0.29 mol) was dissolved in 50 mL water. This solution was added all at once to 2-methyl-3-nitroaniline (20 grams, 0.13 moles) in glacial acetic acid near zero degrees C. The reaction was stirred vigorously with an overhead stirrer. An immediate precipitate occurred upon addition of sodium nitrite solution. The reaction was allowed to reach room temperature and stirred overnight. The precipitate was filtered off and the filtrate was concentrated in vacuo. The dark orange solid was suspended in water, filtered, and dried yielding 14–21 grams of a dark orange solid (99% yield).

B. Preparation of 4-Aminoindazole From 4-Nitroindazole

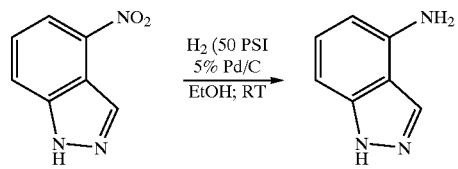

4-Nitroindazole (12 grams) was dissolved in ethanol (300 mL) with warming in a Parr hydrogenation vessel. 5% palladium on carbon (12 grams) was added to the vessel. The reaction vessel was pressurized to 50 PSI and shaken for 1 hour. TLC indicated product formation and loss of starting material. The reaction mixture was filtered over Celite. The catalyst was thoroughly washed with methanol until all product was flushed off. The filtrate was concentrated to a dark gray solid, which was dissolved in ethyl acetate and filtered over a silica pad. The filtrate was concentrated to a brownish solid (9.6 grams, 97% yield).

C. Preparation of 4-Hydroxyindazole From 4-Aminoindazole

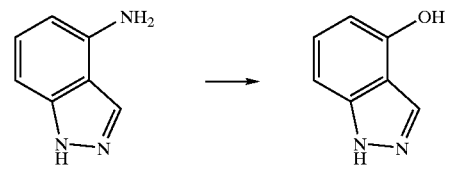

4-Aminoindazole (9.6 grams, 0.072 moles) was dissolved into a glass reaction vessel containing 7.2 grams of concentrated sulfuric acid in 75 mL water. This was sealed into a stainless steel autoclave and heated to 170 degrees C overnight. The reaction mixture contained much black precipitate. The reaction mixture was diluted with ethyl acetate and water into a separatory funnel and partitioned. The aqueous layer was extracted several times with ethyl acetate until all of the product was out of the aqueous fraction. The combined organic fractions were washed with brine, dried.with magnesium sulfate, filtered, and concentrated to a dark brown or black oil. The product was purified by passing it over a silica pad with a 50% ethyl acetate/hexane mixture, resulting in an off-white solid (3.3 grams, 33% yield).

EXAMPLE 2

Preparation of (S)-3-(Indazol-4-yloxy)-1,2-Epoxypropane

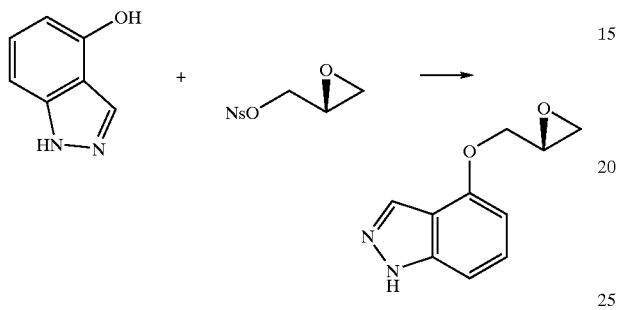

Potassium carbonate (6.8 grams, 0.05 moles) was added to 4-hydroxyindazole (3.3 grams, 0.025 moles), and (2S)-(+)-glycidyl 3-nitrobenzenesulfonate (6.5 grams, 0.025 moles) in acetone at room temperature. The reaction was heated to reflux for 3 hours. TLC (50% ethyl acetate/hexane) indicated that while little starting material was left, a bright-UV product spot appeared in between the starting materials. The reaction was filtered and concentrated to a dark green oil. The oil-was dissolved in ethyl acetate and partitioned with water three times. The organic was dried with magnesium sulfate, filtered, and concentrated to a green oil. The oil was filtered over a silica pad with a 40% ethyl acetate/hexane mixture, resulting in a light green oil (4.1 grams, 88%).

The product is unstable when left at room temperature or in solution for long periods of time and is usually stored in the freezer or used immediately in the epoxide opening reaction. Yield: 50–80%. NMR was consistent with the formation of the desired product.

EXAMPLE 3

Preparation of 4-(2-Methyl-2-Nitropropyl)Phenol

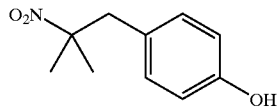

A mixture of 4-hydroxybenzyl alcohol (100.08 grams, 806 mmol), 2-nitropropane (400 mL, 4.45 mol) and diglyme (800 mL) was heated to 38° C. Potassium t-butoxide (45.29 grams, 403.6 mmol) was added, and the mixture was heated to reflux at 132° C. with a Dean-Stark trap. Water began collecting in the trap, and continued at a high rate for approximately 1.5 hours. When water collection slowed (around 2.5 hours), portions of solvent (30–40 mL each) were removed every thirty minutes. During the water collection and solvent removal, the temperature rose from 132° C. to 149° C. After 4 hours less than 1% of the 4-hydroxybenzyl alcohol remained by HPLC analysis. The heating mantle was removed, and the reaction mixture was allowed to cool. When the temperature was 100° C. water (200 mL) was added, and the solution was allowed to cool to room temperature. Solvent was removed on a rotary evaporator under vacuum until 593 grams of solution remained. Water (500 mL) and ethyl acetate (500 mL) were added and the layers were separated (layer separation was poor, but addition of 20% aqueous NaCl was ineffectual). The aqueous layer was extracted with ethyl acetate (200 mL), and the combined organic layers were extracted with 1N HCl (500 mL) and water (300 mL). The organic layer was distilled in vacuo to 261 g of oil to which ethyl acetate was added (160 mL). Heptane (3.4 L) was added rapidly with vigorous stirring for 30 minutes, and the product crystallized to yield a beige solid (112.36 grams, 71% yield, >98% purity by HPLC analysis). Another crop of crystals may be obtained from the filtrate by concentrating and filtering the solids, or by concentrating—and adding heptane to crystallize.

EXAMPLE 4

Preparation of the Acetate Salt of 4-(2-Amino-2-Methylpropyl)phenol

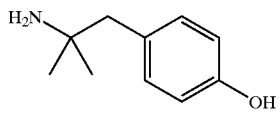

A one-gallon high-pressure reactor was charged with 4-(2-methyl-2-nitropropyl)phenol (120 grams, 614 mmol), acetic acid (35.2 mL, 614 mmol), 5% Palladium on carbon (24 grams) wetted with 2B3 ethanol (60 mL), and methanol (1230 mL). The mixture was heated to 50° C. with agitation (600 rpm), and the reactor was purged with $N_2$ and pressurized to 50 psi with $H_2$. After 15.5 hours the reactor was purged with $N_2$, and the cooled mixture was filtered. The filter cake was washed with methanol, and the filtrate was concentrated to 514 grams of slurry on a rotary evaporator. To this slurry was added ethyl acetate (2 Liters) with vigorous agitation. After stirring for 1 hour, the resulting crystals were filtered and washed with a small amount of ethyl acetate. The product was dried overnight in a 45° C. vacuum oven to yield 118.83 grams (86%) of product as small white needles (mp 211–216° C. dec). This material was determined to be 99% pure by HPLC analysis. While another 9.00 g of material was obtained from the mother liquor, it was found to be only 88% pure.

EXAMPLE 5

Preparation of (4-(2-amino-2-methylpropyl) phenoxy)-4-(methylsulfonyl)benzene

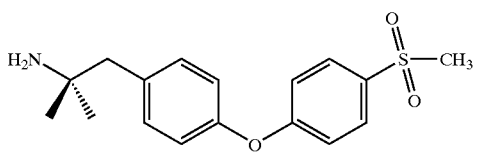

A mixture of 4-(2-amino-2-methylpropyl)phenol acetic acid salt (45.06 grams, 200 mmol), powdered $K_2CO_3$ (69.1 grams, 500 mmol), 4-chloro-methylsulfonylbenzene (200 mmol), DMAC (622 mL) and iso-octane (70 mL) was slowly heated to reflux at 140° C. 4-(2-Amino-2-methylpropyl)phenol acetic acid salt was prepared according to the Procedures described in Example 3 and 4.

A water trap filled with iso-octane was used to collect water formed in the reaction, and reflux was maintained for 5.5 hours. The mixture was allowed to cool to room temperature, and the solids were filtered and washed with ethyl acetate. The filtrate was concentrated in vacuo to give a solid which was dissolved in ethyl acetate (500 mL). To this solution was added water (800 mL), 1N HCl (200 mL) and methanol (50 mL). The pH of this mixture was adjusted to 7.2 with concentrated HCl, and the aqueous layer was separated and washed with methyl t-butyl either (500 mL). The product was crystallized by addition of 10N NaOH (20 mL), which raised the pH to 11. This pH was maintained by addition of 10N NaOH as needed during the course of the crystallization (90 minutes). Melting point: 85.3–85.5° C. NMR was consistent with the desired product.

EXAMPLE 6

Preparation of Compound 5

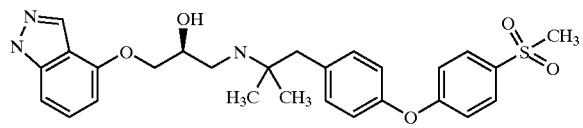

A stirred mixture of an (S)-3-(4-indazolyloxy)-1,2-epoxypropane (2.5 grams, 0.013 moles), prepared as described in Example 2, and (4-(2-amino-2-methylpropyl) phenoxy)-4-(methylsulfonyl)benzene (4.5 grams, 0.014 moles), prepared as described in Example 5, in anhydrous methanol (75 mL) was refluxed for 24 hours. The reaction mixture was then concentrated in vacuo and purified by flash chromatography over silica (2% ammonium hydroxide, 15% methanol, 83% ethyl acetate) to give a white foam (1.8 grams, 31% yield).

Other compounds of the present invention were prepared by reacting (S)-3-(4-indazoyloxy)-1,2-epoxypropane with the appropriate amine starting material according to the procedures described above. The amine starting materials were prepared according to procedures described in Example 5 using the appropriately substituted chlorobenzene or chloropyridine (6-chloronicotinamide for Compound 1; 2-chloronicotinamide for Compound 2; 2-chloro-5-cyano-pyridine for Compound 3; and N-[6-cloro-3-pyridylcarbonyl)morpholine for Compound 4. N-[6-chloro-3-pyridylcarbonyl)morpholine was prepared by reacting 6-chloro-3-pyridylcarboxylic acid with thionyl chloride to form the corresponding acid chloride and then amidating with morpholine.

Compounds were characterized by electro spray ionization mass spectrometry (ESIMS). Molecular ion peaks were 476.2 (calculated molecular weight 475.55 amu) for Compound 1; 476.0 (calculated molecular weight 475.55 amu) for Compound 2; 458.0 (calculated molecular weight 457.53 amu) for Compound 3; 546.0 (calculated molecular weight 545.64 amu) for Compound 4; and 510.0 (calculated molecular weight 509.62 amu) for Compound 5.

EXAMPLE 7

Intravenous Administration of the Compounds of the Present Invention to Cattle

Intravenous administration of the compounds of the present invention to cattle was found to increase the level of serum non-esterified fatty acid, and to decrease the level of serum urea nitrogen. Angus/Angus cross steer calves, both heifers and steers, weighing approximately 282 pounds (128 kg) initially to 788 pounds (358 kg) over the course of these studies, were placed in pens at 5 calves per pen. The cattle were acclimated to the pens for at least 1 week prior to initiating the study.

Calves were fed ad libitum twice daily, (approximately 6–15 pounds (2.7–6.8 kg)/day). During the treatment day, in the A.M. period, the feeding times were staggered to ensure that all animals were fed approximately one hour before the treatments were administered. During the P.M. treatment period, the cattle were fed immediately after receiving the P.M. injection.

After taking a pretreatment (T=0) blood sample from each animal, 40 µg per kilogram of a test compound was administered intravenously in the jugular vein at 6:30 A.M. and 2:30 P.M. Each test compound was administered at a concentration of 1.00–1.25 mg/ml in a treatment vehicle that was a 50/50 mixture of polyethylene glycol 200/water.

A blood sample was taken at fifteen minutes post-treatment (T+15 min). The calves were returned to their respective pens until their next treatment, approximately eight hours later. The next morning at 6:30 A.M. a blood sample was collected from all calves at 24 hours post-treatment (T+24h). All blood samples were analyzed for the non-esterified fatty acid level (NEFA) and serum urea nitrogen level (SUN). The post-treatment NEFA and SUN levels in each individual animal were compared with the levels found before treatment. The results are shown in Table 1.

TABLE 1

| STRUCTURE | ΔNEFA* 15 Min. | ΔNEFA** 24 Hours | Δ % SUN*** 24 Hours |
|---|---|---|---|
| Vehicle only | ~0 | ~0 | ~0 |
| Compound 1 | 554.4 | 820.9 | −28.7 |

TABLE 1-continued

| STRUCTURE | ΔNEFA* 15 Min. | ΔNEFA** 24 Hours | Δ % SUN*** 24 Hours |
|---|---|---|---|
| Compound 2 | 141.2 | 742.4 | −39.3 |
| Compound 3 | 269.4 | 1069.3 | −24.7 |
| Compound 4 | 194.8 | 1251.8 | −40.1 |
| Compound 5 | 397.3 | 1541.9 | −25.4 |

*The increase in NEFA (μmol/liter) in the blood of animals treated with the indicated test compound compared with baseline (T = 0) NEFA value for each individual at 15 minutes post treatment (ΔNEFA = T + 15 min NEFA value − T = 0 NEFA value). Values presented are the mean of five animals.
**The increase in NEFA (μmol/liter) in the blood of animals treated with the indicated test compound compared with baseline (T = 0) NEFA value for each individual 24 hours post treatment (ΔNEFA = T + 24 h NEFA value − T = 0 NEFA value). Values presented are the mean of five animals.
***The percent decrease in SUN in the blood of animals treated with the indicated test compound at 24 hours post treatment compared with the baseline (T = 0) SUN value for each individual. Values presented are the mean of five animals.

$$\%\Delta SUN = \frac{(T + 24\text{ h }SUN) - (T = 0\ SUN)}{T = 0\ SUN} \times 100\%$$

From the data presented in Table 1, it can be seen that Compounds 1–5 possess both anabolic and lipolytic activity.

EXAMPLE 8

Oral Administration of the Compounds of the Present Invention to Cattle

The indazolyloxy propanolamines of the present invention were found to provide longer acting anabolic activity when administered orally to cattle than obtained with other aryloxy propanolamines. In the present example, fifteen head of Angus/Angus cross steer calves, weighing approximately 484 pounds (220 kg) initially to 604 pounds (274 kg) by the end of these three trials, were placed in pens in the cattle facilities, at 5 calves per pen. Standard vaccination and coccidal control were administered.

Calves were fed ad libitum twice daily, approximately 10–15 pounds (4.54–6.81 kg)/day. The feeding times were staggered once treatment was initiatedto ensure that all calves were fed approximately one hour before the treatments were administered and blood samples were obtained.

During the A.M. treatment period, the cattle were prevented from returning to feed until the +180 minute blood sample had been collected.

Treatments were administered once a day via oral gavage. The treatments contained 1 mg of test compound per kilogram body weight and were administered in a 50/50 PEG 200/water vehicle, followed with a flush of 20 mls of 50/50 PEG 200/water.

A baseline blood sample (T=0) was taken immediately before the oral gavage treatment was administered. At 90 minutes post-treatment (T+90 min) another blood sample was taken. The cattle were returned to their designated pens until 180 minutes post-treatment (T+180 min), when a third blood sample was collected. The calves were not allowed access to their feed until they had completed the 180 minute blood sample. Additional blood samples were collected from each calf at 24 and 48 hours post treatment.

All blood samples were taken from the jugular vein and placed into serum tubes. Serum was assayed on an IL Monarch analyzer. Blood samples were collected pretreatment (T=0), 90 minutes post-treatment (T+90 min), 180 minutes post-treatment (T+180 min) and 24 hours post-treatment (T+24 h) and 48 hours post-treatment (T+48 h). Sera at T=0, T+90 min, T+180 min, T+24 h, and T+48 h were analyzed for NEFA and SUN. The results are shown below in Table 2.

TABLE 2

| STRUCTURE | Δ % SUN*<br>24 Hours | Δ % SUN<br>48 Hours | ΔNEFA*<br>24 Hours |
|---|---|---|---|
| Vehicle only | ~0 | ~0 | ~0 |
| 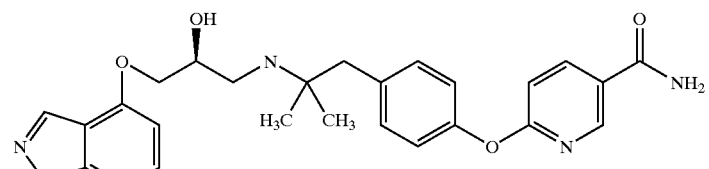<br>Compound 1 | −38 | −32 | 329 |
| 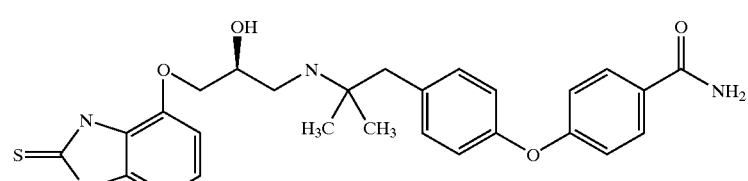 | −8 | −12 | 17 |
| 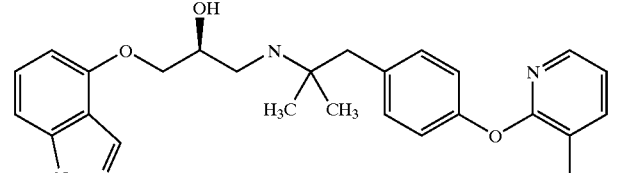<br>Compound 2 | −56 | −57 | 825 |
| 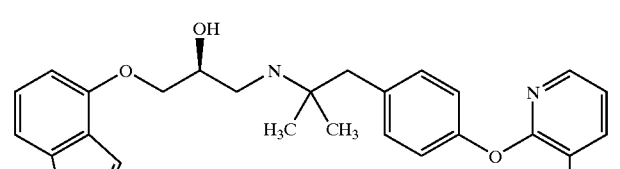 | −42 | −30 | −30 |
| 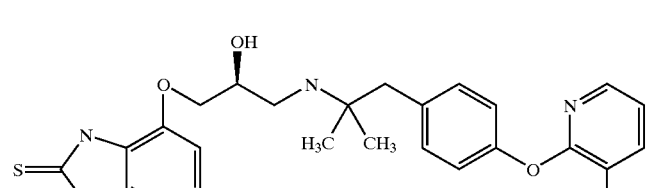 | −17 | −13 | 101 |

TABLE 2-continued

| STRUCTURE | Δ % SUN* 24 Hours | Δ % SUN** 48 Hours | ΔNEFA*** 24 Hours |
|---|---|---|---|
| [structure: 2-oxo-benzimidazol-4-yloxy-CH2-CH(OH)-CH2-NH-C(CH3)2-CH2-C6H4-O-pyridine-3-carboxamide] | −22 | −19 | 10 |
| [structure: indazol-4-yloxy-CH2-CH(OH)-CH2-NH-C(CH3)2-CH2-C6H4-O-pyridine-CN] Compound 3 | −58 | −57 | 349 |
| [structure: indol-4-yloxy-CH2-CH(OH)-CH2-NH-C(CH3)2-CH2-C6H4-O-pyridine-CN] | −55 | −40 | 63 |
| [structure: 2-oxo-benzimidazol-7-yloxy-CH2-CH(OH)-CH2-NH-C(CH3)2-CH2-C6H4-O-pyridine-CN] | 2 | 5 | 18 |
| [structure: indazol-5-yloxy-CH2-CH(OH)-CH2-NH-C(CH3)2-CH2-C6H4-O-pyridine-morpholine carbonyl] Compound 4 | −47 | −48 | 1129 |
| [structure: indol-5-yloxy-CH2-CH(OH)-CH2-NH-C(CH3)2-CH2-C6H4-O-pyridine-morpholine carbonyl] | −45 | −28 | −47 |

TABLE 2-continued

| STRUCTURE | Δ % SUN* 24 Hours | Δ % SUN** 48 Hours | ΔNEFA*** 24 Hours |
|---|---|---|---|
| [structure] | −18 | −15 | 6 |
| [structure] Compound 5 | −33 | −60 | 1216 |
| [structure] | −1 | −5 | 37 |
| [structure] | −10 | −6 | −6 |

*The percent decrease in SUN in the blood of animals treated with the indicated test compound at 24 hours post treatment compared with the baseline (T = 0) SUN value for each individual. Values presented are the mean of five animals.
**The percent decrease in SUN in the blood of animals treated with the indicated test compound at 48 hours post treatment compared with the baseline (T = 0) SUN value for each individual. Values presented are the mean of five animals.
***The increase in NEFA (μmol/liter) in the blood of animals treated with the indicated test compound compared with baseline (T = 0) NEFA value for each individual 24 hours post treatment (ΔNEFA = T + 24 h NEFA value − T = 0 NEFA value). Values presented are the mean of five animals.
% Δ SUN is calculated as described in Example 7.

From the data presented in Table 2, it is seen that indazolyloxy propanolamines of Compounds 1–5 maintain anabolic activity for at least forty-eight hours and lipolytic activity for at least twenty-four hours when administered orally to cattle, whereas the anabolic and lipolytic activity of other aryloxy propanolamines is maintained for considerably shorter time periods.

EXAMPLE 9

Anabolic Effects of Compounds 1 and 5 When Administered to Chickens

Approximately 1500 Peterson-Hubbard day-old male chicks were used in a randomized, complete block design with 6 treatments (Control; Clenbuterol at 1 PPM; Compound 1 at 3 and 15 PPM (mg/kg feed); and Compound 5 at 3 and 15 PPM) using pen location in the barn as the blocking factor. Treatments were randomly allotted to pens within each block for a total of 6 pens per block and 6 blocks in the wing. Each treatment consisted of 6 pens, with 10 birds per pen, during the experimental period.

Day-of-age birds were obtained from Pine Manor Hatchery in Goshen, Ind. Approximately 40 birds per pen were setup at random upon receipt. On day 30 of the growout period, all birds were weighed and the 15 birds closest to the block mean were selected. These birds were allowed to acclimate until day 35 of age. On this day, all remaining birds were weighed again, and the 10 birds/pen closest to the block mean were chosen for the treatment phase. Birds were provided ad libitum access to feed and water throughout the trial. All birds were fed a 23% crude protein corn-soy ration from day 1 until day 18 of age. The feed was changed to a 20% crude protein corn-soy ration for day 18 to day 49. The treatment feed was mixed using the 20% crude protein corn-soy basal ration. Treatments were administered in the feed from day 35 through day 49. Feed consumption was calculated over the entire 14 day treatment period. Birds were weighed at trial completion (day 49), and transported to Purdue University meat laboratory for slaughter and carcass measurements on day 50. Weights of the hot carcass, fat pad, and viscera were taken on all animals. Weights of the bone-in, skin-on breast, and the bone-in, skin-on leg quarters were taken only on the control treatment and the high doses of both experimental compounds.

Compound 1 showed an increase in weight gain of 11.50% (P=0.0009) over control for the 15 PPM treatment.

The same compound at the 3 PPM treatment showed a 3.54% (P=0.2209) increase over control. Compound 5 showed a similar response to Compound 1 in that it showed a 8.85% (P=0.0065) increase over control at the 15 PPM treatment. The 3 PPM treatment of Compound 5 gave a 2.65% (P=0.5491) increase over control. The Clenbuterol treated birds showed a 3.54% (P=0.2090) increase over control during the 14 day treatment period. Compounds 1 and 5 tended to improve feed efficiency by 4.67% (P=0.1956) and 3.27% (P=0.3652), respectively, in the 15 PPM treatment. In the 3 PPM treatment, feed efficiency was not improved for either compound. Clenbuterol treated animals did not show an improvement in feed conversion versus control.

The following formulation examples are illustrative only and are not intended to limit the scope of the invention in any way. "Active Ingredient," of course, means a compound of Structural Formula I or a physiologically acceptable salt or solvate thereof.

EXAMPLE 10

Premix for Chickens

| Ingredient | % by weight |
|---|---|
| Active Ingredient | 25 |
| Ground Corn | 74 |
| Sodium Chloride | 1 |
|  | 100 |

EXAMPLE 11

Premix for Ruminants

| Ingredient | % by weight |
|---|---|
| Active Ingredient | 30 |
| Ground yellow corn | 60 |
| Alfalfa meal | 10 |
|  | 100 |

EXAMPLE 12

Premix for Swine

| Ingredient | % by weight |
|---|---|
| Active Ingredient | 10 |
| Soybean mill run | 88 |
| Mineral oil | 2 |
|  | 100 |

The above ingredients are blended to uniformity to provide a dry flowable premix that can be admixed with a typical animal feed ration at a rate to provide about 20 ppm of active ingredient in the final feed ration. For example, the premix can be added to the following swine grower ration for convenient oral administration of the Active Ingredient to swine.

| Ingredient | % by weight | Lbs/Ton |
|---|---|---|
| Corn, yellow, ground | 76.70 | 1534 |
| Soybean Oil Meal, solvent extracted, dehulled | 19.35 | 387 |
| Calcium Carbonate | 1.20 | 24 |
| Dicalcium Phosphate, feed grade | 1.20 | 24 |
| Salt (sodium chloride) | 0.50 | 10 |
| Trace mineral premix, AN-03[1] | 0.10 | 2 |
| Swine Vitamin Premix, SW-03[2] | 0.65 | 13 |
| Vitamin A Premix, 3M USP units/lb.[3] | 0.05 | 1 |
| Methionine Hydroxy Analogue, 93% | 0.20 | 4 |
| Selenium Premix[4] | 0.005 | 1 |
|  | 100.00 | 2000 |

[1]Each Kg of premix contains: 50 g. manganese as manganese sulfate; 100 g. zinc as zinc carbonate; 50 g. iron as ferrous sulfate; 5 g. copper as copper oxide; 1.5 g. iodine as potassium iodide and 150 g. maximum and 130 g. minimum calcium as calcium carbonate.

[2]Each Kg of premix contains: 77,161 IU Vitamin D2; 2,205 IU Vitamin E; 411 mg. riboflavin; 1,620 mg. pantothenic acid; 2,205 mg. niacin; 4.4 mg. Vitamin B12; 441 mg. Vitamin K; 19,180 mg. choline; 110 mg. folic acid; 165 mg. pyridoxine; 110 mg. thiamine; 22 mg. biotin.

[3]Each Kg of premix contains 6,613,800 IU Vitamin A.

[4]Each Kg of premix contains 200 mg. of selenium as sodium selenite.

EXAMPLE 13

Feed Ration for Lambs

| Ingredient | Percent | Lbs/T |
|---|---|---|
| Yellow corn | 61.00 | 1220.0 |
| Corn cobs | 20.00 | 400.0 |
| Alfalfa Meal, dehydrated | 5.40 | 108.0 |
| Soybean oil meal | 8.00 | 160.0 |
| Urea, feed grade | 0.50 | 10.0 |
| Molasses, cane | 3.00 | 60.0 |
| Dicalcium phosphate | 0.43 | 8.6 |
| Salt | 0.30 | 6.0 |
| Calcium carbonate | 0.14 | 2.3 |
| Trace mineral premix[1] | 0.03 | 0.6 |
| Vitamin A + $D_3$ Premix[2] | 0.10 | 2.0 |
| Vitamin E Premix[3] | 0.10 | 2.0 |
| Active Ingredient | 1.00 | 20.0 |
|  | 100.00 | 2000.0 |

[1]Trace mineral premix contains: 2.5% manganese as manganese oxide, 0.07% iodine as potassium iodide, 0.3% cobalt as cobalt carbonate, 0.5% copper as copper oxide, and 20.0% zinc as zinc sulfate.

[2]Each pound of vitamin A and $D_3$, premix contains 2,000,000 USP units Vitamin A and 225,750 USP units Vitamin $D_3$.

[3]Each pound of Vitamin E premix contains 20,000 IU Vitamin E.

EXAMPLE 14

Broiler Finisher Ration

| Ingredients | % by weight | Lbs/T |
|---|---|---|
| Ground yellow corn | 66.40 | 1328.00 |
| Animal-vegetable fat | 1.53 | 30.60 |
| Corn Glut. meal (60%) | 4.00 | 80.00 |
| Soybean meal (48%) | 19.19 | 383.80 |
| Fish meal-menhaden | 2.50 | 50.00 |
| Dicalcium phosphate | 1.01 | 34.20 |
| Feather meal-Hydr. | 2.50 | 50.00 |
| Ground limestone | 0.83 | 16.60 |
| Salt | 0.30 | 6.00 |
| Vitamin Premix[1] | 0.50 | 10.00 |
| Trace mineral premix[2] | 0.10 | 2.00 |
| Methionine Hyd. Anal. | 0.15 | 3.00 |
| Lysine HCl | 0.29 | 5.80 |
|  | 100.00 | 2000.00 |

[1]Vitamin premix provides 3000 IU of vitamin A, 900 ICU of vitamin $D_3$, 40 mg of vitamin E, 0.7 mg of vitamin K, 1000 mg of choline, 70 mg of niacin, 4 mg of pantothenic acid, 4 mg of riboflavin, 100 mcg of vitamin $B_{12}$, 100 mcg of biotin and 125 mg of ethoxyquin per kg of complete feed.

[2]Trace mineral premix provides 75 mg of manganese, 50 mg of zinc, 25 mg of iron and 1 mg of iodine per kg of complete feed Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A compound represented by the following structural formula:

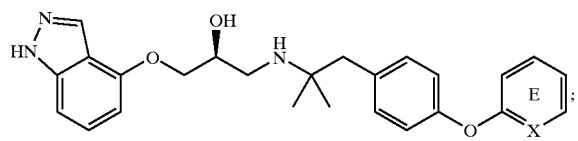

and physiologically acceptable salts thereof, wherein:
Ring E is unsubstituted or substituted with —CN, —CONH$_2$, —SO$_2$CH$_3$, —SO$_2$NH$_2$,

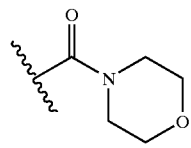

or

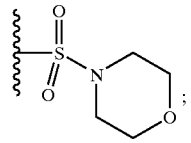

and
X is —CH— or —N—;
provided that Ring E is not substituted in the position meta to —X— and ortho to the carbon bonded to oxygen with —CONH$_2$ or

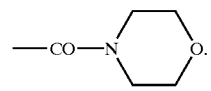

2. The compound of claim 1 wherein Ring E is substituted with —CN, —CONH$_2$, —SO$_2$CH$_3$, or

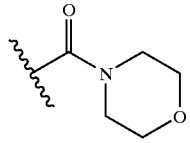

provided that Ring E is not substituted in the position meta to —X— and ortho to the carbon bonded to oxygen with —CONH$_2$ or

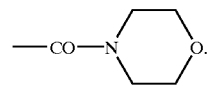

3. A method of increasing the quantity of meat or improving the quality of meat obtained from a livestock animal, comprising administering to the animal an effective amount of a compound represented by the following structural formula:

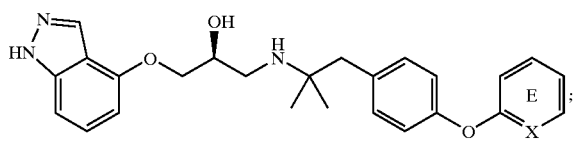

and physiologically acceptable salts thereof, wherein: Ring is unsubstituted or substituted with —CN, —CONH$_2$, —SO$_2$CH$_3$, —SO$_2$NH$_2$,

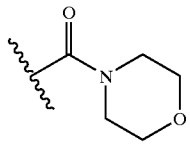

or

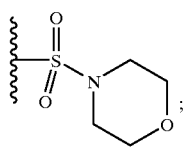

and
X is —CH— or —N—;
provided that Ring E is not substituted in the position meta to —X— and ortho to the carbon bonded to oxygen with —CONH$_2$ or

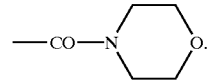

4. The compound of claim 2 represented by the following structural formula:

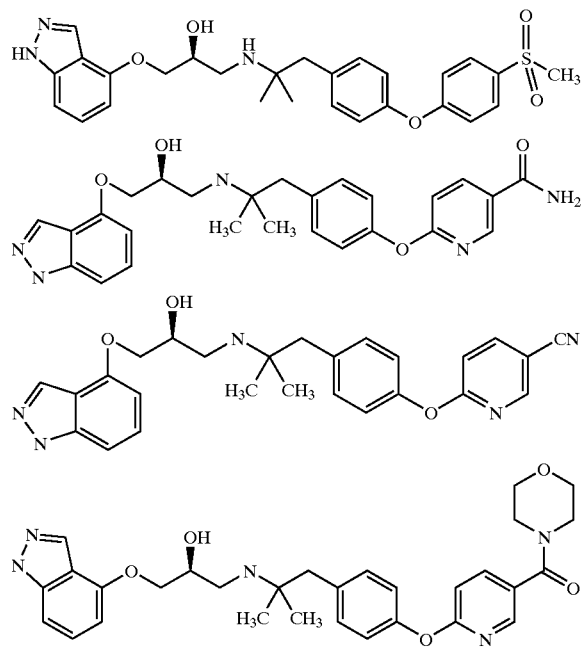

or a physiologically acceptable salt thereof.

5. The compound of claim 4 represented by the following structural formula:

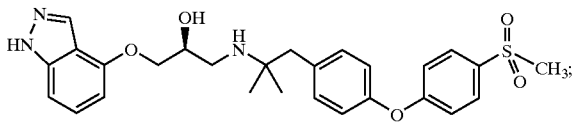

or a physiologically acceptable salt thereof.

6. The method of claim 3 wherein the growth of the livestock animal is promoted, the efficiency of feed.

7. The method of claim 6 wherein the animal is avian.

8. The method of claim 7 wherein the animal is a chicken, turkey, goose or duck.

9. A pharmaceutical composition, which comprises as an active ingredient a compound as claimed in claim 1 together with a physiologically acceptable diluent or carrier.

10. An animal feed premix comprising a compound of claim 1 or a physiologically acceptable salt or solvate thereof, in association with a suitable carrier therefor.

11. An animal feed composition comprising a compound of claim 1 or a physiologically acceptable salt or solvate thereof, in association with a suitable carrier therefor.

12. A pharmaceutical composition, which comprises as an active ingredient a compound as claimed in claim 2 together with a physiologically acceptable diluent or carrier.

13. A pharmaceutical composition, which comprises as an active ingredient a compound as claimed in claim 4 together with a physiologically acceptable diluent or carrier.

14. A pharmaceutical composition, which comprises as an active ingredient a compound as claimed in claim 5 together with a physiologically acceptable diluent or carrier.

15. An animal feed premix comprising a compound as claimed in claim 2 or a pharmaceutically acceptable salt or solvate thereof, in association with a suitable carrier therefor.

16. An animal feed premix comprising a compound as claimed in claim 4 or a physiologically acceptable salt or solvate thereof, in association with a suitable carrier therefor.

17. An animal feed premix comprising a compound as claimed in claim 5 or a physiologically acceptable salt or solvate thereof, in association with a suitable carrier therefor.

18. An animal feed composition comprising a compound as claimed in claim 2 or a physiologically acceptable salt or solvate thereof, in association with a suitable carrier therefor.

19. An animal feed composition comprising a compound as claimed in claim 4 or a physiologically acceptable salt or solvate thereof, in association with a suitable carrier therefor.

20. An animal feed composition comprising a compound as claimed in claim 5 or a physiologically acceptable salt or solvate thereof, in association with a suitable carrier therefor.

* * * * *